US011944651B2

(12) United States Patent
Takata et al.

(10) Patent No.: US 11,944,651 B2
(45) Date of Patent: Apr. 2, 2024

(54) ANTIMICROBIAL AND ANTIVIRAL AGENT, ANTIMICROBIAL AND ANTIVIRAL MEMBER, AND METHOD FOR PRODUCING ANTIMICROBIAL AND ANTIVIRAL AGENT

(71) Applicant: Murata Manufacturing Co., Ltd., Nagaokakyo (JP)

(72) Inventors: Masachika Takata, Nagaokakyo (JP); Hirofumi Sunahara, Nagaokakyo (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 79 days.

(21) Appl. No.: 17/468,765

(22) Filed: Sep. 8, 2021

(65) Prior Publication Data
US 2021/0401899 A1 Dec. 30, 2021

Related U.S. Application Data

(63) Continuation of application No. 16/218,763, filed on Dec. 13, 2018, now abandoned, which is a (Continued)

(30) Foreign Application Priority Data

Jun. 13, 2016 (JP) .................. 2016-117443

(51) Int. Cl.
*A61K 35/747* (2015.01)
*A61K 9/06* (2006.01)
(Continued)

(52) U.S. Cl.
CPC ............... *A61K 35/74* (2013.01); *A61K 9/06* (2013.01); *A61K 35/747* (2013.01);
(Continued)

(58) Field of Classification Search
CPC .... A61K 35/74; A61K 35/747; A61K 36/282; A61K 9/06; C12N 1/04; C12N 1/20;
(Continued)

(56) References Cited

U.S. PATENT DOCUMENTS

2014/0356338 A1 12/2014 Park et al.
2019/0125806 A1 5/2019 Takata et al.

FOREIGN PATENT DOCUMENTS

CN 104171178 A 12/2014
JP 2006-248902 A 9/2006
(Continued)

OTHER PUBLICATIONS

Yoshida, Rika et al., "Quality control of Japanese mugwort-fermented broth by monitoring the microorganisms," Abstracts of the 59th Annual Meeting of the Society for Biotechnology, Hiroshima, Japan, Sep. 25-27, 2007, p. 180, Abstract No. 2H15-3.
(Continued)

*Primary Examiner* — David W Berke-Schlessel
*Assistant Examiner* — Trent R Clarke
(74) *Attorney, Agent, or Firm* — Sterne, Kessler, Goldstein & Fox P.L.L.C.

(57) ABSTRACT

The present invention aims to provide an antimicrobial and antiviral agent which comprises a naturally occurring component as an active ingredient and is effective against microbes including various classes of fungi and viruses. In one aspect of the present invention, provided is an antimicrobial and antiviral agent comprising *Lactobacillus* derived from *Artemisia indica* var. *maximowiczii*.

13 Claims, 7 Drawing Sheets

Related U.S. Application Data continuation of application No. PCT/JP2017/021563, filed on Jun. 12, 2017.

(51) Int. Cl.

| | |
|---|---|
| *A61K 35/74* | (2015.01) |
| *A61K 36/232* | (2006.01) |
| *A61K 36/282* | (2006.01) |
| *A61P 31/04* | (2006.01) |
| *A61P 31/10* | (2006.01) |
| *A61P 31/12* | (2006.01) |
| *A61P 31/16* | (2006.01) |
| *C12N 1/04* | (2006.01) |
| *C12N 1/20* | (2006.01) |

(52) U.S. Cl.
CPC .......... *A61K 36/232* (2013.01); *A61K 36/282* (2013.01); *A61P 31/04* (2018.01); *A61P 31/10* (2018.01); *A61P 31/12* (2018.01); *A61P 31/16* (2018.01); *C12N 1/04* (2013.01); *C12N 1/20* (2013.01)

(58) Field of Classification Search
CPC ......... A61P 31/12; A61P 31/04; A61P 31/10; A61P 31/16
See application file for complete search history.

(56) References Cited

FOREIGN PATENT DOCUMENTS

| | | |
|---|---|---|
| JP | 2007-308504 A | 11/2007 |
| JP | 2010-195778 A | 9/2010 |
| JP | 2010-215641 A | 9/2010 |
| JP | 2010-246398 A | 11/2010 |
| JP | 2011-140453 A | 7/2011 |
| JP | 2012-147759 A | 8/2012 |
| JP | 2013-53089 A | 3/2013 |
| JP | 2013-150598 A | 8/2013 |
| JP | 2013-188196 A | 9/2013 |
| JP | 2014-230541 A | 12/2014 |
| JP | 2015-193619 A | 11/2015 |
| JP | 2016-097039 A | 5/2016 |
| KR | 10-2009-0083505 A | 8/2009 |
| KR | 10-2012-0005686 A | 1/2012 |
| WO | WO 97/36603 A1 | 10/1997 |
| WO | WO 2014/172758 A1 | 10/2014 |
| WO | WO 2015/140299 A1 | 9/2015 |

OTHER PUBLICATIONS

Office action for JP Patent Appl. No. 2021-008788, dated Dec. 15, 2021, by the Japan Patent Office, Tokyo, Japan.
Office action for JP Patent Appl. No. 2021-008839, dated Dec. 15, 2021, by the Japan Patent Office, Tokyo, Japan.
International Search Report (ISR) for PCT/JP2017/021563; I.A. fd: Jun. 12, 2017; dated Jul. 18, 2017 from the Japan Patent Office, Tokyo, Japan.
International Preliminary Report on Patentability (IPRP) for PCT/JP2017/021563; I.A. fd: Jun. 12, 2017; dated Dec. 18, 2018, by the International Bureau of WIPO, Geneva, Switzerland.
Shokryazdan, P et al., "Probiotic potential of Lactobacillus strains with antimicrobial activity against some human pathogenic strains," Biomed Res Int. 2014;2014:927268. doi: 10.1155/2014/927268. Epub Jul. 3, 2014, 16 pages.
Inglin, RC et al., "High-throughput screening assays for antibacterial and antifungal activities of Lactobacillus species," J Microbiol Methods. Jul. 2015;114:26-9. doi: 10.1016/j.mimet.2015.04.011. Epub Apr. 30, 2015.
Park, JY et al., "Characteristic of alkylated chalcones from Angelica keiskei on influenza virus neuraminidase inhibition," Bioorg Med Chem Lett. Sep. 15, 2011;21(18):5602-4. doi: 10.1016/j.bmcl.2011. 06.130. Epub Jul. 20, 2011.
Yong, J et al., "Advances in studies on the rupestonic acid derivatives as anti-influenza agents," Mini Rev Med Chem. Feb. 2013;13(2):310-5.
Oba, T et al., "Ashitaba Defensin: An Anti-Fungal Peptide From Angelica Keiskei," Journal of the Pharmaceutical Society of Japan Oct. 1, 2006; 126(Supp. 3), abstracts of The First Symposium on Pharmaceutical Food Science, Oct. 26-27, 2006, Osaka Prefecture, pp. 54-55.
Partial supplementary European search report including the Provisional Opinion Accompanying the Partial Search Result, for EP Application No. 17 813 247.8, Communication dated Dec. 10, 2019, European Patent Office, Munich, Germany.
Badwaik, LS et al., "Production and purification of anti-bacterial biometabolite from wild-type Lactobacillus, isolated from fermented bamboo shoot: future suggestions and a proposed system for secondary metabolite onsite recovery during continuous fermentation," Appl Biochem Biotechnol. Feb. 2015;175(4):1915-25. doi: 10.1007/s12010-014-1415-z. Epub Nov. 29, 2014.
Leal-Sánchez, MV et al., "Fermentation profile and optimization of green olive fermentation using Lactobacillus plantarum LPCO10 as a starter culture," Food Microbiology 20(4), Aug. 2003, 421-430.
Yildirim, Z et al., "Characterization of Buchnericin LB Produced by Lactobacillus buchneri LB," Turk J Biol 25(1), Jan. 2001, 73-82.
Notice of Reasons for Refusal, for JP patent application No. 2018-204221, dated Nov. 1, 2019, the Japan Patent Office, Tokyo, Japan.
Notice of Reasons for Refusal, for JP patent application No. 2018-523882, dated Oct. 30, 2019, the Japan Patent Office, Tokyo, Japan.
Yoshida, Y. et al., Quality control of Japanese mugwort-fermented broth by monitoring the microorganisms, The 59th meeting of the Japan Society of Biotechnology, Sep. 25-27, 2007, Hiroshima, Japan, p. 180, Abstract No. 2HI5-3 presented Sep. 26, 2007.
Ohhira, I. et al., "The isolation and identification of lactic acid bacteria from naturally fermented wild plants and fruits," Japanese J of Dairy and Food Science 36(2): A69-A75 (1987).
The extended European search report including the supplementary European search report and the European search opinion, for EP App. No. 17813247.8, dated Mar. 18, 2020, European Patent Office, Munich Germany.
"Notice of Reasons for Refusal," Office Action for JP Appl. No. 2018-204221, dated Jan. 7, 2020 from the Japan Patent Office, Tokyo, Japan.
Yoshida, R. et al., "Quality Control of Japanese Mugwort-Fermented Broth by Monitoring the Microorganisms," Abstract No. 2H15-3, presented at the 59th Annual Meeting of the Society of Biotechnology of Japan, Hiroshima, Japan, Sep. 25-27, 2007, p. 180.
Robert H. Silverman, Viral Encounters with 2',5'-Oligoadenylate Synthetase and RNase L during the Interferon Antiviral Response, 2007, Journal of Virology, vol. 81, No. 23, pp. 12720-12729 (Year: 2007).
Hiraki Ishikawa et al., Oral Administration of Heat-Killed Lactobacillus plantarum Strain b240 Protected Mice against Salmonella enterica Serovar Typhimurium, 2010, Bioscience, Biotechnology, and Biochemistry, vol. 74, No. 7, pp. 1338-1342 (Year: 2010).

| Species of bacteria | |
|---|---|
| Lactobacillus parafarraginis | 2207 |
| Lactobacillus parabuchneri | 653 |
| Lactobacillus buchneri | 540 |
| Lactobacillus harbinensis | 266 |
| Not determined | 5392 |

| Species of bacteria | |
|---|---|
| Lactobacillus vini | 12601 |
| Acetobacter papayae | 1549 |
| Paenibacillus endophyticus | 433 |
| Lactobacillus nagelii | 183 |
| Not determined | 1054 |

008504
ANTIMICROBIAL AND ANTIVIRAL AGENT, ANTIMICROBIAL AND ANTIVIRAL MEMBER, AND METHOD FOR PRODUCING ANTIMICROBIAL AND ANTIVIRAL AGENT

CROSS-REFERENCE TO RELATED APPLICATIONS

The following applications are incorporated herein by reference: PCT/JP2017/021563 (filed Jun. 12, 2017) and JP 2016-117443 (filed Jun. 13, 2016).

BACKGROUND OF THE INVENTION

Technical Field

The present invention relates to an antimicrobial and antiviral agent, an antimicrobial and antiviral member, and a method of manufacturing the antimicrobial and antiviral agent.

Background Art

Some lactic acid bacteria are known to counteract pathogenic microbes harmful to humans and animals. For example, Patent Literature 1 discloses the use of *Lactobacillus pentosus* derived from *Alpinia zerumbet* for eradicating *Helicobacter pylori*. However, Patent Literature 1 discloses that a concentrated fermentation liquor of *Alpinia zerumbet* has no effect on candida.

Patent Literature 2 discloses that *Lactobacillus reuteri* produces an antimicrobial substance called reuterin and can inhibit proliferation of bacteria including salmonellae and some fungi. Patent Literature 2 also discloses the use of *Lactobacillus fermentum* for the treatment and prevention of skin disorders. Patent Literature 2 further discloses the use of *Lactobacillus reuteri* for the prevention or treatment of skin disorders caused by pathogenic microbes such as *Staphylococcus aureus, Streptococcus pyogenes*, and *Propionibacterium acnes*, and for the prevention or treatment of methicillin-resistant *Staphylococcus aureus* (MRSA) infection.

Patent Literature 3 discloses that *Lactobacillus plantarum* can suppress proliferation of Gram-negative bacteria such as *Escherichia coli, Klebsiella pneumoniae, Pseudomonas aeruginosa*, and *Staphylococcus aureus* and Gram-positive bacteria but cannot suppress proliferation of fungi such as *Candida albicans* and *Candida parapsilosis*.

Patent Literature 4 discloses that *Lactobacillus casei* KE01 can reduce *Escherichia coli* over several weeks. Patent Literature 5 discloses that *Lactobacillus gasseri* can reduce *Salmonella enteritidis*. Patent Literature 6 discloses that a biofilm consisting of yeast and *Lactobacillus plantarum* ML11-11 can reduce *Bacillus subtilis*.

Patent Literature 7 discloses that *Lactobacillus pentosus* can suppress proliferation of candida. However, Patent Literature 7 does not disclose that *Lactobacillus pentosus* can reduce candida.

CITATION LIST

Patent Literature

Patent Literature 1: Japanese Patent Laid-Open No. 2015-193619
Patent Literature 2: Japanese Patent Laid-Open No. 2014-230541
Patent Literature 3: Japanese Patent Laid-Open No. 2010-215641
Patent Literature 4: Japanese Patent Laid-Open No. 2010-195778
Patent Literature 5: Japanese Patent Laid-Open No. 2012-147759
Patent Literature 6: Japanese Patent Laid-Open No. 2013-150598
Patent Literature 7: Japanese Patent Laid-Open No. 2007-308504

BRIEF SUMMARY OF THE INVENTION

Technical Problem

Although alcohols may be used as an antimicrobial agent, some bacteria that form spores, such as *Bacillus cereus, Bacillus subtilis*, and *Bacillus subtilis* var. *natto*, are alcohol-resistant. Alcohols can cause side effects such as a rash and skin irritation. In addition, antimicrobial agents comprising a synthetic compound as an active ingredient may irritate the affected areas and cause symptoms of contact dermatitis that itch and are painful. Therefore, it is desirable to develop an antimicrobial and antiviral agent that contains a naturally occurring component as an active ingredient and is effective against microbes including various classes of fungi and viruses. The present invention, which has been achieved in light of such circumstances, aims to provide an antimicrobial and antiviral agent that comprises a naturally occurring component as an active ingredient and is effective against microbes including various classes of fungi and viruses, an antimicrobial and antiviral member, and a method of manufacturing the antimicrobial and antiviral agent.

Solution to Problem

The antimicrobial and antiviral agent according to one aspect of the present invention includes *Lactobacillus* derived from *Artemisia indica* var. *maximowiczii*. The antimicrobial and antiviral agent according to one aspect of the present invention also includes a secretion from *Lactobacillus* derived from *Artemisia indica* var. *maximowiczii*. Further, the antimicrobial and antiviral agent according to one aspect of the present invention includes *Lactobacillus*, wherein the *Lactobacillus* is at least one species selected from the group consisting of *parafarraginis, parabuchneri, buchneri, harbinensis, vini*, and *nagelii*. Further, the antimicrobial and antiviral agent according to one aspect of the present invention also includes a secretion from *Lactobacillus*, wherein the *Lactobacillus* is at least one species selected from the group consisting of *parafarraginis, parabuchneri, buchneri, harbinensis, vini*, and *nagelii*. Furthermore, the antimicrobial and antiviral member according to one aspect of the present invention includes a member and the antimicrobial and antiviral agent disposed on a surface of the member. A method of manufacturing the antimicrobial and antiviral agent according to one aspect of the present invention includes fermenting a plant to provide a fermentation liquor containing *Lactobacillus*.

Advantageous Effects of Invention

The present invention provides an antimicrobial and antiviral agent that comprises a naturally occurring component as an active ingredient and is effective against microbes including various classes of fungi and viruses, an antimicrobial and antiviral member, and a method of manufacturing the antimicrobial and antiviral agent.

DESCRIPTION OF EMBODIMENTS

Figure 1:
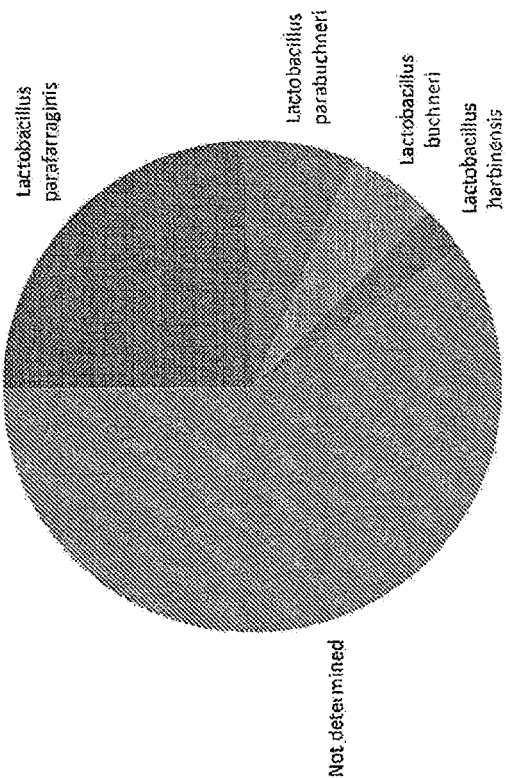
FIG. 1 is a graph and table showing results of analyzing bacteria contained in the fermentation liquor according to Example 1.

Embodiments of the present invention will be now described in detail. It should be understood that embodiments as described below illustrate a device or method for embodying technical idea of the present invention and thus the technical idea of the present invention does not limit combination of constituent members to those as described below. The technical idea of the present invention may make various changes within the scope of the claims.

First Embodiment

The antimicrobial and antiviral agent according to the first embodiment of the present invention includes at least one selected from the group consisting of *Lactobacillus* and a secretion from *Lactobacillus*. *Lactobacillus* is a species of lactobacilli and is a Gram-positive facultative anaerobe. *Lactobacillus* ferments sugar to produce lactic acid. Although *Lactobacillus* inhabits the living bodies of animals including human, *Lactobacillus* derived from plants is preferable for the *Lactobacillus* according to the first embodiment.

For example, the *Lactobacillus* according to the first embodiment can be extracted from fermented plants. Examples of the plants include, but not limited to, *Artemisia indica* var. *maximowiczii*, *Angelica keiskei*, *Isodonis Herba*, and *Theobroma cacao*. Examples of *Lactobacillus* derived from *Artemisia indica* var. *maximowiczii* include *Lactobacillus parafarraginis*, *Lactobacillus parabuchneri*, *Lactobacillus buchneri*, and *Lactobacillus harbinensis*. Examples of *Lactobacillus* derived from *Angelica keiskei* include *Lactobacillus vini* and *Lactobacillus nagelii*. The antimicrobial and antiviral agent according to the first embodiment may include a plurality of *Lactobacillus* species.

The antimicrobial and antiviral agent according to the first embodiment can reduce the number of fungi (molds). The antimicrobial and antiviral agent according to the first embodiment can reduce for example 80% or more, 85% or more, 90% or more, or 95% or more of the fungi within 24 hours. Examples of the fungi include, but not limited to, *Trichophyton*, *Candida*, *Cryptococcus*, and *Aspergillus*. The antimicrobial and antiviral agent according to the first embodiment can be used as a therapeutic agent for mycosis. The mycosis includes, but not limited to, trichophytosis, candidosis, cryptococcosis, and aspergillosis.

The antimicrobial and antiviral agent according to the first embodiment can reduce the number of Gram-negative and Gram-positive bacteria. The antimicrobial and antiviral agent according to the first embodiment can reduce for example 80% or more, 85% or more, 90% or more, or 95% or more of the Gram-negative and Gram-positive bacteria within 24 hours. The Gram-negative bacteria include, but not limited to, *Escherichia coli*, *Salmonella enterica*, *Vibrio parahaemolyticus*, *Klebsiella pneumoniae*, *Pseudomonas aeruginosa*, and the like. The Gram-positive bacteria include, but not limited to, methicillin-resistant *Staphylococcus aureus* (MRSA), *Bacillus cereus* which forms spores, *Bacillus subtilis*, and the like. The antimicrobial and antiviral agent according to the first embodiment can be used as a disinfectant against Gram-negative and Gram-positive bacteria.

The antimicrobial and antiviral agent according to the first embodiment can reduce the number of viruses. The antimicrobial and antiviral agent according to the first embodiment can reduce for example 80% or more, 85% or more, 90% or more, or 95% or more of the viruses within 24 hours. The viruses include enveloped viruses which are viruses with envelope and non-enveloped viruses which are viruses without envelope. The viruses also include DNA and RNA viruses.

DNA viruses with envelope include, but not limited to, human herpes virus, vaccinia virus, hepatitis B virus, and the like.

RNA viruses with envelope include, but not limited to, influenza virus, SARS coronavirus, RS virus, mumps virus, Lassa virus, dengue virus, rubella virus, human immunodeficiency virus, measles virus, hepatitis C virus, Ebola virus, yellow fever virus, Japanese encephalitis virus, and the like.

DNA viruses without envelope include, but not limited to, adenovirus, B19 virus, papovavirus, human papillomavirus, and the like.

RNA viruses without envelope include, but not limited to, norovirus, polioviruses, echovirus, hepatitis A virus, hepatitis E virus, rhinovirus, astrovirus, rotavirus, coxsackievirus, enterovirus, sapovirus, and the like.

The antimicrobial and antiviral agent according to the first embodiment can be used as a disinfectant against viruses.

The antimicrobial and antiviral agent according to the first embodiment includes an effective amount of *Lactobacillus* and/or an effective amount of a secretion from *Lactobacillus*. The effective amount refers to an amount necessary to exert an antimicrobial or antiviral effect and thus will be appropriately determined depending on microbes, viruses, and symptoms of interest. The antimicrobial and antiviral agent according to the first embodiment includes *Lactobacillus*, for example, in a concentration of 0.001 wt % or more, 0.005 wt % or more, or 0.01 wt % or more. The antimicrobial and antiviral agent according to the first embodiment also includes *Lactobacillus*, for example, in a concentration of 20 wt % or less, 15 wt % or less, or 10 wt % or less but may include *Lactobacillus* in a higher concentration. However, the viscosity tends to increase with increasing the concentration of *Lactobacillus*.

The *Lactobacillus* contained in the antimicrobial and antiviral agent according to the first embodiment may be a living bacterium or a bacterium killed, for example, by heat treatment. Therefore, the antimicrobial and antiviral agent according to the first embodiment may include a killed bacterium of *Lactobacillus*. The *Lactobacillus* may be a dried bacterial product. The killed bacterium or dried bacterial product of *Lactobacillus* also has an antimicrobial and antiviral effect. Moreover, the killed bacterium or dried bacterial product of *Lactobacillus* can be easily transported and stored over an extended period.

The antimicrobial and antiviral agent according to the first embodiment may be, for example, a liquid, a cream, an ointment, a plaster, a gel, a wax, or a spray. The antimicrobial and antiviral agent according to the first embodiment is also administered in, for example, a disinfectant, a skin external medicine including a therapeutic agent for application, an eye drop, and an internal medicine. The antimicrobial and antiviral agent according to the first embodiment can be applied to, for example, human skin including fingers and toes, hair, mouth cavity, eyeball, and the like. The antimicrobial and antiviral agent according to the first embodiment can also be applied to, for example, cooking devices, walls and floors of buildings such as hospitals, and furniture such as a desk.

The antimicrobial and antiviral agent according to the first embodiment may appropriately include, in addition to *Lactobacillus*, components blended for cosmetics and pharmaceuticals depending on its purpose such as a liquid fat, a solid fat, a wax, a hydrocarbon, a higher fatty acid, a higher alcohol, an ester, a silicone, an anionic surfactant, a cationic surfactant, an amphoteric surfactant, a nonionic surfactant, a humectant, a water-soluble polymer, a thickening agent, a film-forming agent, a sequestering agent, a lower alcohol, a polyhydric alcohol, saccharides, amino acids, organic amines, a pH adjusting agent, skin nutrients, vitamins, an antioxidant, a flavor, a powder, a coloring material, and water.

The antimicrobial and antiviral agent according to the first embodiment may appropriately include depending on its purpose, in addition to *Lactobacillus*, an antimicrobial substance or an antiviral substance.

*Lactobacillus* and a secretion from *Lactobacillus* to be used as an active ingredient in the antimicrobial and antiviral agent according to the first embodiment can reduce microbes including various classes of fungi and viruses causing various diseases such as food poisoning. *Lactobacillus* and a secretion from *Lactobacillus* to be used as an active ingredient in the antimicrobial and antiviral agent according to the first embodiment can also reduce *Bacillus cereus* which forms alcohol-resistant spores.

Furthermore, *Lactobacillus*, which is a naturally occurring lactic acid bacterium, to be used as an active ingredient in the antimicrobial and antiviral agent according to the first embodiment has no or little deleterious effects including side effects and thus is safe when administered to humans. Also, for example the antimicrobial and antiviral agent according to the first embodiment to be given as a skin external medicine has no or little deleterious effects including side effects in the event of accidental ingestion by infants, children, or elderly persons because *Lactobacillus* is an edible lactic acid bacterium and can be easily degraded by digestive enzymes in the intestinal tract. The same holds true for the secretion of *Lactobacillus*.

The antimicrobial and antiviral agent according to the first embodiment is produced by fermenting a plant to provide a fermentation liquor containing *Lactobacillus*. When the plant is fermented, salts and sugars such as molasses are added to the plant. The fermentation is performed at a temperature of, for example, 30° C. The resulting fermentation liquor has a hydrogen ion exponent (pH) of about 4.0. A secretion from *Lactobacillus* may be extracted from the fermentation liquor.

The resulting fermentation liquor may be heated to kill *Lactobacillus* contained in the fermentation liquor. The fermentation liquor may also be spray dried to provide a dried bacterial product of *Lactobacillus*. The dried bacterial product can be prepared by freeze-drying (lyophilization), hot-air drying, or the like.

Furthermore, the resulting fermentation liquor, bacterium of *Lactobacillus*, or dried bacterial product of *Lactobacillus* may be added to soymilk which may be fermented to provide a soymilk fermentation liquor. The soymilk fermentation liquor also has an antimicrobial and antiviral effect.

Second Embodiment

In the second and subsequent embodiments, description of similarity to the first embodiment is omitted and only points differing from the first embodiment will be described. In particular, similar actions and effects through a similar configuration are not mentioned in detail in each embodiment.

The antimicrobial and antiviral member according to the second embodiment includes a member and the antimicrobial and antiviral agent according to the first embodiment disposed on a surface of the member. The member is solid and is made of a material including, but not limited to, for example, metal, resin, glass, ceramic, and wood. For example, when the antimicrobial and antiviral member according to the second embodiment is produced, the antimicrobial and antiviral agent according to the first embodiment is blended into a paint, a dye, a pigment, various resins, a synthetic rubber, a latex, a film, a fiber, or the like and the material having the antimicrobial and antiviral agent blended is applied, disposed, or laminated onto a surface of the member.

Examples of the concentration of the antimicrobial and antiviral agent blended in the material may include, but not limited to, 0.001 wt % or more, 0.005 wt % or more, or 0.01 wt % or more and 20 wt % or less, 15 wt % or less, or 10 wt % or less.

EXAMPLES

Embodiments of the present invention will be described below. However, the present invention is of course not limited to the following Examples.

Example 1

*Lactobacillus* Derived From *Artemisia indica* Var. *maximowiczii*

It appears that in leaves of *Artemisia indica* var. *maximowiczii*, the number of lactic acid bacteria reaches the maximum for an hour before and after sunrise, i.e., a total of 2 hours throughout the day. It also appears that lactic acid bacteria will decrease and photosynthetic bacteria will increase except for this time period. Accordingly, the tip of *Artemisia indica* var. *maximowiczii* leaf of about 20 cm long was taken during those 2 hours described above. The first pickle barrel with inside covered with a plastic bag was immediately charged with 6.3 kg of taken *Artemisia indica* var. *maximowiczii* leaves and 3.2 kg of molasses and 0.6 kg of crude salt were sprinkled on the *Artemisia indica* var. *maximowiczii* leaves before closing the plastic bag to seal. A weight was placed on the plastic bag to pickle the *Artemisia indica* var. *maximowiczii* leaves.

Several days after the level of the pickle juice exceeded the level of *Artemisia indica* var. *maximowiczii* leaves, the weight was removed. Next, the second pickle barrel was charged with 10 L of chlorine-free water for rinse and the pickled *Artemisia indica* var. *maximowiczii* leaves and 10 kg of the pickle juice were added to the water. Additionally, the third pickle barrel was provided and a wire gauze filter was placed on the opening of the third pickle barrel. The pickled *Artemisia indica* var. *maximowiczii* leaves were taken from the second pickle barrel in small portions while being kneaded and washed by hand. The *Artemisia indica* var. *maximowiczii* leaves were squeezed by lightly pressing them with the palm to the wire gauze filter on the opening of the third pickle barrel to obtain pickle juice.

After all the *Artemisia indica* var. *maximowiczii* leaves were squeezed, the pickle juice left in the second pickle juice was filtered through the wire gauze filter. Next, molasses (Hateruma brown sugar) and crude salt were added to final concentrations of 10 wt % and 3 wt % respectively to the pickle juice in the third pickle barrel and dissolved in the pickle juice. The ambient temperature of the third pickle barrel was then increased to about 30° C. to start fermentation. At first, effervescence was observed with large bubbles which were then gradually changed to small bubbles, and finally the effervescence subsided. About 1 week after the effervescence subsided, pH was near 3.8. The pickle juice at that time was used as an *Artemisia indica* var. *maximowiczii* fermentation liquor. A portion of the resulting *Artemisia indica* var. *maximowiczii* fermentation liquor was heated at 70° C. for 30 minutes to kill bacteria and provide a heat-treated *Artemisia indica* var. *maximowiczii* fermentation liquor.

A non-heat-treated *Artemisia indica* var. *maximowiczii* fermentation liquor was analyzed with a next generation sequencer (MiSeq, Illumina, Inc.), and the *Artemisia indica* var. *maximowiczii* fermentation liquor contained *Lactobacillus parafarraginis*, *Lactobacillus parabuchneri*, *Lactobacillus buchneri*, *Lactobacillus harbinensis*, and the like, as shown in FIG. 1. It is noted that the next generation sequencer may be called high-throughput sequencer. Numerical values in the table in FIG. 1 represent the number of bacterial species contained in the *Artemisia indica* var. *maximowiczii* fermentation liquor.

Example 2

*Lactobacillus* Derived From *Angelica keiskei*

It appears that in *Angelica keiskei*, the number of lactic acid bacteria reaches the maximum for an hour before and after sunrise, i.e., a total of 2 hours throughout the day. It also appears that lactic acid bacteria will decrease and photosynthetic bacteria will increase except for this time period. Accordingly, leaves and stems of *Angelica keiskei* sprouts were taken during the 2 hours. The first pickle barrel with inside covered with a plastic bag was immediately charged with 6.3 kg of taken *Angelica keiskei* and 3.2 kg of molasses and 0.6 kg of crude salt were sprinkled on the *Angelica keiskei* before closing the plastic bag to seal. A weight was placed on the plastic bag to pickle *Angelica keiskei*.

Several days after the level of the pickle juice exceeded the level of *Angelica keiskei*, the weight was removed. Next, the second pickle barrel was charged with 10 L of chlorine-free water for rinse and the pickled *Angelica keiskei* and 10 kg of the pickle juice were added to the water. Additionally, the third pickle barrel was provided and a wire gauze filter was placed on the opening of the third pickle barrel. The pickled *Angelica keiskei* was taken from the second pickle barrel in small portions while being kneaded and washed by hand. The *Angelica keiskei* was squeezed by lightly pressing it with the palm to the wire gauze filter on the opening of the third pickle barrel to obtain pickle juice.

After all the *Angelica keiskei* was squeezed, the pickle juice left in the second pickle juice was filtered through the wire gauze filter. Next, molasses and crude salt were added to final concentrations of 10 wt % and 3 wt % respectively to the pickle juice in the third pickle barrel and dissolved in the pickle juice. The ambient temperature of the third pickle barrel was then increased to about 30° C. to start fermentation. At first, effervescence was observed with large bubbles which were then gradually changed to small bubbles, and finally the effervescence subsided. About 1 week after the effervescence subsided, pH was near 4.0. The pickle juice at that time was used as an *Angelica keiskei* fermentation liquor. A portion of the resulting *Angelica keiskei* fermentation liquor was heated at 70° C. for 30 minutes to kill bacteria and provide a heat-treated *Angelica keiskei* fermentation liquor.

Figure 2:
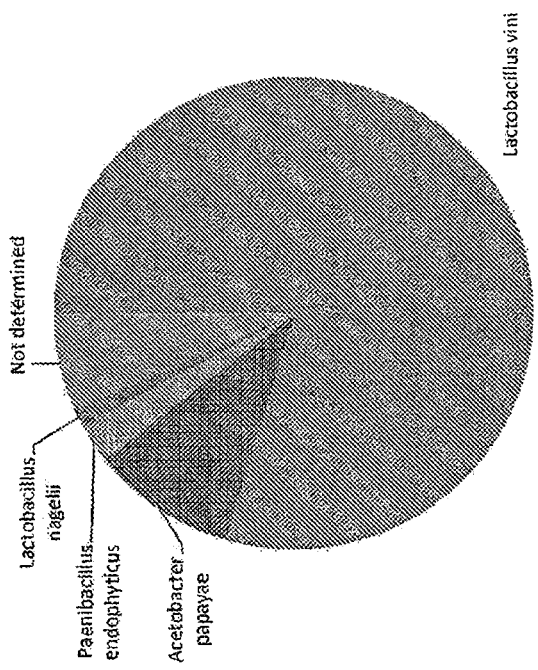
FIG. 2 is a graph and table showing results of analyzing bacteria contained in the fermentation liquor according to Example 2.

A non-heat-treated *Angelica keiskei* fermentation liquor was analyzed with a next generation sequencer (MiSeq, Illumina, Inc.), and the *Angelica keiskei* fermentation liquor contained species *vini*, *nagelii*, and the like, as shown in FIG. 2. It is noted that numerical values in the table in FIG. 2 represent the number of bacterial species contained in the *Angelica keiskei* fermentation liquor.

Example 3

SOYMILK Fermentation Liquor Prepared with *Lactobacillus*

Soymilk was heat-sterilized for about 30 minutes by heating it to 70° C. To the heat-sterilized soymilk was added the non-heat-treated *Artemisia indica* var. *maximowiczii* fermentation liquor prepared in Example 1 to a final concentration of about 10 wt % and stirred thoroughly. Soymilk containing the non-heat-treated *Artemisia indica* var. *maximowiczii* fermentation liquor was then fermented at 37° C. for 24 hours. After fermentation, solid substances were removed by filtration to provide a soymilk fermentation liquor containing *Lactobacillus*.

Example 4

Antimicrobial Effect of *Lactobacillus*

*Staphylococcus aureus* and MRSA were provided as Gram-positive cocci; *Bacillus subtilis* and *Bacillus cereus* were provided as Gram-positive bacilli; *Escherichia coli*, *Salmonella enterica*, *Vibrio parahaemolyticus*, and *Klebsiella pneumoniae* were provided as Gram-negative cocci; and *Pseudomonas aeruginosa* was provided as a Gram-negative bacillus.

Figure 3:
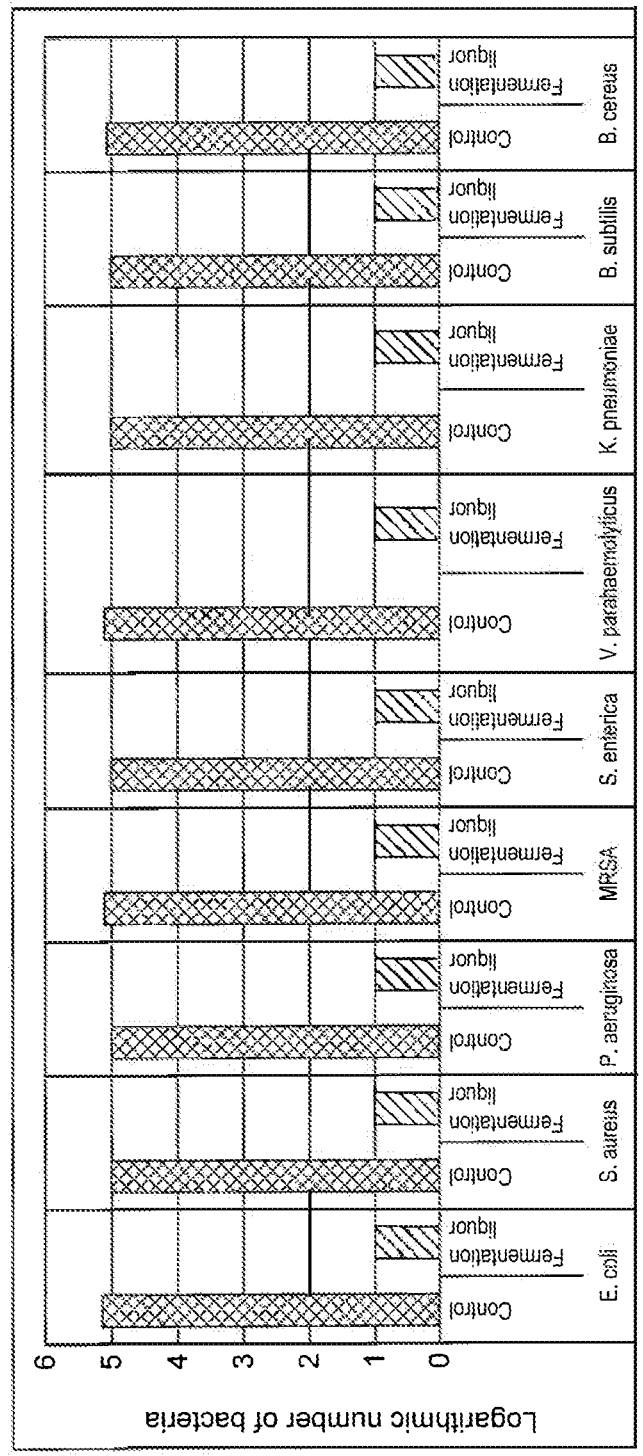
FIG. 3 is a graph and table showing antimicrobial effect of the fermentation liquor according to Example 4.

10 mL of the soymilk fermentation liquor containing *Lactobacillus* prepared in Example 1 was inoculated with 0.1 mL of a bacterial suspension containing any of the bacteria as described above in a concentration of $10^7$/mL and allowed to act at 25° C. The viable cell count of the inoculated bacterium was measured over time for 24 hours. As a control, 10 mL of 1/15 mol/L in a concentration of phosphate buffer, pH 7.2 was inoculated with 0.1 mL of the bacterial suspension and allowed to act at 25° C. The viable cell count of the inoculated bacterium was measured over time for 24 hours. As a result, as shown in FIG. 3, the soymilk fermentation liquor containing *Lactobacillus* decreased all the species of bacteria provided within 24 hours.

Example 5

Antifungal Effect of *Lactobacillus*

Figure 4:
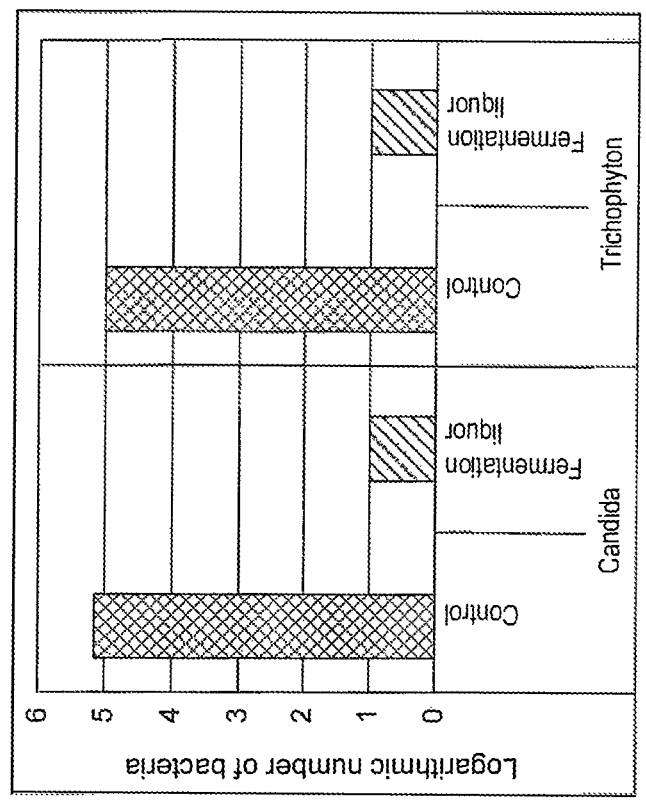
FIG. 4 is a graph and table showing antifungal effect of the fermentation liquor according to Example 5.

*Trichophyton* and *Candida* were provided as fungi. 10 mL of the soymilk fermentation liquor containing *Lactobacillus* prepared in Example 1 was inoculated with 0.1 mL of a fungal suspension containing *Trichophyton* or *Candida* in a concentration of $10^7$/mL and allowed to act at 25° C. The viable cell count of the inoculated fungus was measured over time for 24 hours. As a control, 10 mL of 1/15 mol/L in a concentration of a phosphate buffer, pH 7.2 was inoculated with 0.1 mL of the fungal suspension and allowed to act at 25° C. The viable cell count of the inoculated fungus was measured over time for 24 hours. As a result, as shown in FIG. 4, the soymilk fermentation liquor containing *Lactobacillus* decreased the *Trichophyton* and *Candida* provided within 24 hours.

Example 6

Antiviral Effect of *Lactobacillus*

The culture supernatant containing influenza virus A (H1N1) was provided as an enveloped virus. The culture supernatant containing norovirus (feline calicivirus) was also provided as a non-enveloped virus. These virus-containing culture supernatants were 10-fold serially diluted with purified water. Subsequently, an antiviral test was performed at room temperature to determine 50% Tissue Culture Infectious Dose (TCID50). The antiviral test was performed at Japan Food Research Laboratories.

Figure 5:
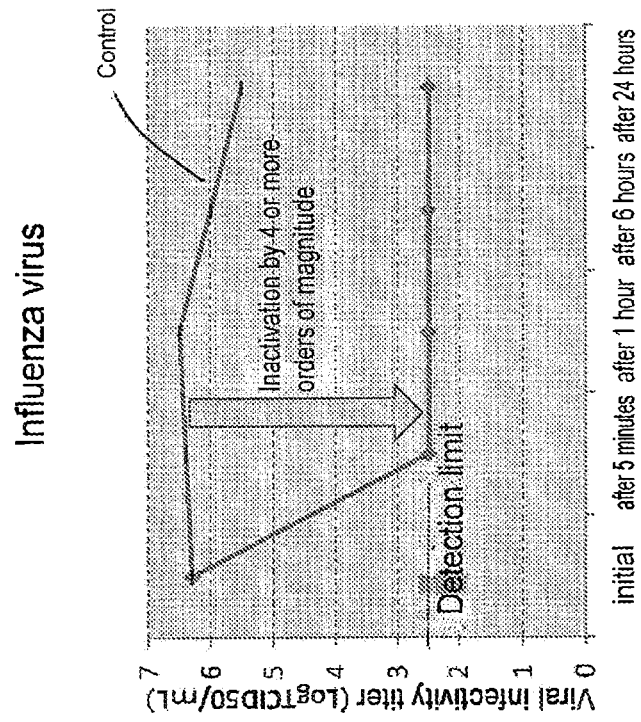
FIG. 5 is a graph and table showing antiviral effect of the fermentation liquor according to Example 6.
Figure 6:
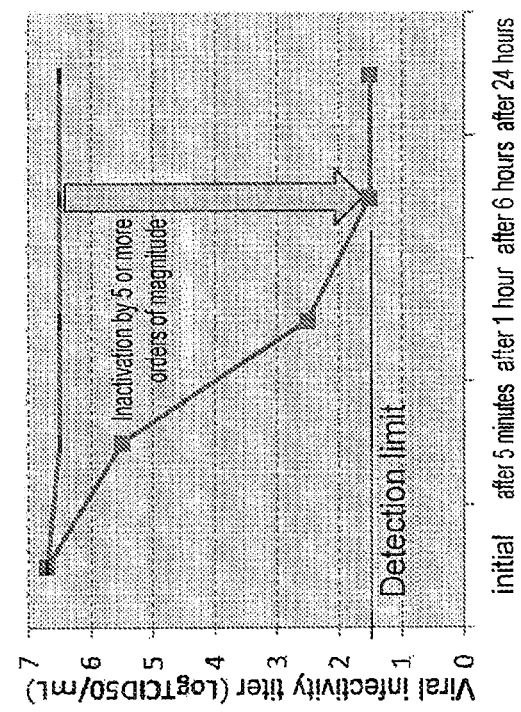
FIG. 6 is a graph and table showing antiviral effect of the fermentation liquor according to Example 6.

As a result, as shown in FIG. 5, the soymilk fermentation liquor containing *Lactobacillus* decreased the infectivity titer of influenza virus within 1 hour. As shown in FIG. 6, the soymilk fermentation liquor containing *Lactobacillus* also decreased the infectivity titer of norovirus within 24 hours.

Example 7

Anti-Trichophyton Effect of *Lactobacillus*

Figure 7:
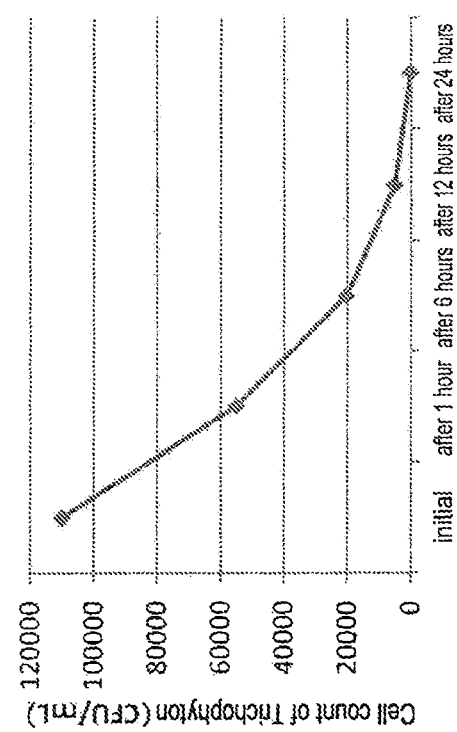
FIG. 7 is a graph and table showing anti-Trichophyton effect of the fermentation liquor according to Example 7.

The non-heat-treated *Artemisia indica* var. *maximowiczii* fermentation liquor prepared in Example 1 was spray-dried to provide a dried fungus of *Lactobacillus*. The dried fungus was suspended in water and glycerin to a concentration of 10 parts by weight to provide a *Lactobacillus* suspension according to Example 7. The *Lactobacillus* suspension was added to *Trichophyton* and colony-forming unit (CFU) of *Trichophyton* was measured, which revealed that, as shown in FIG. 7, the *Lactobacillus* suspension killed *Trichophyton* within 24 hours.

Each of the embodiments and Examples as described above is intended to facilitate understanding of the present invention but not to limit the interpretation of the present invention. The present invention may be altered or modified without departing from the spirit thereof and includes equivalents thereof. That is to say, the design of each of the embodiments and Examples appropriately changed by those skilled in the art is within the scope of the present invention as long as it includes a feature of the present invention. For example, each element comprised in each of the embodiments and Examples is not limited to the exemplified elements and may be appropriately changed. Any of the embodiments and Examples is also exemplary and thus, needless to say, components described in other embodiments may be partially substituted or combined. These partial substitution and combination are also within the scope of the present invention as long as they include a feature of the present invention.

What is claimed is:

1. A method for reducing Gram-positive bacteria, Gram-negative bacteria, fungi and virus comprising administering an antimicrobial and antiviral agent to a subject, the agent comprising *Lactobacillus* derived from *Artemisia indica* var. *maximowiczii* or a secretion from the *Lactobacillus* derived from *Artemisia indica* var. *maximowiczii*, wherein the agent is a fermentation product of soymilk and *Artemisia indica* var. *maximowiczii*.

2. The method according to claim 1, wherein the agent is a liquid, a cream, an ointment, a plaster, a gel, a wax, or a spray.

3. The method according to claim 1, wherein the agent is obtained by fermenting a mixture of the soymilk and fermented *Artemisia indica* var. *maximowiczii*.

4. The method according to claim 1, wherein the Gram-positive bacteria includes Gram-positive cocci and Gram-positive bacilli.

5. The method according to claim 4, wherein the Gram-positive cocci includes *Staphylococcus aureus* and methicillin-resistant *Staphylococcus aureus* (MRSA).

6. The method according to claim 4, wherein the Gram-positive bacilli includes *Bacillus subtilis* and *Bacillus cereus*.

7. The method according to claim 1, wherein the Gram-negative bacteria includes Gram-negative cocci and Gram-negative bacillus.

8. The method according to claim 7, wherein the Gram-negative cocci includes *Escherichia coli, Salmonella enterica, Vibrio parahaemolyticus*, and *Klebsiella pneumoniae*.

9. The method according to claim 7, wherein the Gram-negative bacillus includes *Pseudomonas aeruginosa*.

10. The method according to claim 1, wherein the fungi includes *Trichophyton* and *Candida*.

11. The method according to claim 1, wherein the virus includes enveloped virus and non-enveloped virus.

12. The method according to claim 11, wherein the enveloped virus includes influenza virus.

13. The method according to claim 11, wherein the non-enveloped virus includes norovirus.

* * * * *